United States Patent
Kim

(10) Patent No.: US 11,166,970 B2
(45) Date of Patent: Nov. 9, 2021

(54) COMPOSITION FOR PREVENTING OR TREATING NEUROLOGICAL DISORDER COMPRISING AUCUBIN

(71) Applicant: University-Industry Cooperation Group of Kyung Hee University, Gyeonggi-do (KR)

(72) Inventor: Yunhee Kim, Seoul (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 0 days.

(21) Appl. No.: 16/763,969

(22) PCT Filed: Nov. 14, 2018

(86) PCT No.: PCT/KR2018/013903
§ 371 (c)(1),
(2) Date: Jul. 28, 2020

(87) PCT Pub. No.: WO2019/098674
PCT Pub. Date: May 23, 2019

(65) Prior Publication Data
US 2020/0360410 A1    Nov. 19, 2020

(30) Foreign Application Priority Data
Nov. 14, 2017    (KR) .................. 10-2017-0151768

(51) Int. Cl.
*A61K 31/7048*    (2006.01)
*A61P 25/00*    (2006.01)

(52) U.S. Cl.
CPC .......... *A61K 31/7048* (2013.01); *A61P 25/00* (2018.01)

(58) Field of Classification Search
None
See application file for complete search history.

(56) References Cited

U.S. PATENT DOCUMENTS 9,375,457 B2 * 6/2016 Chen ................. A61K 36/756

FOREIGN PATENT DOCUMENTS

| CN | 105596357 A | * | 5/2016 | ......... A61K 31/7048 |
|---|---|---|---|---|
| CN | 105596357 A | | 5/2016 | |
| JP | H0995445 A | * | 4/1997 | ............. A61K 31/35 |
| KR | 10-1414133 B | | 7/2014 | |
| KR | 10-2015-0123152 A | | 11/2015 | |
| KR | 10-2015-0136012 A | | 12/2015 | |
| KR | 10-1912544 B1 | | 10/2018 | |

OTHER PUBLICATIONS

Guo, H., Shi, F., Li, M., Liu, Q., Yu, B., & Hu, L. (2015). Neuroprotective effects of Eucommia ulmoides Oliv. and its bioactive constituent work via ameliorating the ubiquitin-proteasome system. BMC Complementary and Alternative Medicine, 15(1), 151. (Year: 2015).*
Yamazaki, M., Hirota, K., Chiba, K., & Mohri, T. (1994). Promotion of neuronal differentiation of PC12h cells by natural lignans and iridoids. Biological and Pharmaceutical Bulletin, 17(12), 1604-1608. (Year: 1994).*
Xue, H., Jin, L., Jin, L., Zhang, P., Li, D., Xia, Y., . . . & Xu, Y. (2008). Neuroprotection of aucubin in primary diabetic encephalopathy. Science in China Series C: Life Sciences, 51(6), 495-502. (Year: 2008).*
Pedersen AL, Pettygrove S, Lu Z, Andrews J, Meaney FJ, Kurzius-Spencer M, et al. (Aug. 2017). "DSM Criteria that Best Differentiate Intellectual Disability from Autism Spectrum Disorder". Child Psychiatry and Human Development. 48 (4): 537-545. (Year: 2017).*
Eghorn et al., "Positive allosteric modulation of the GHB high-affinity binding site by the GABAA receptor modulator monastrol and the flavonoid catechin," European J. of Pharmacology, 740:570-577, 2014.
Kang et al., "Research advances in pharmacology of aucubin and aucubigenin," Zhongguo Zhong Yao Za Zhi, 32(24):2585-2587, 2007.
Kim et al., "Aucubin promotes neurite outgrowth in neural stem cells and axonal regeneration in sciatic nerves," Exp. Neurobiol. 23(3):238-345, 2014.
International Search Report and Written Opinion of the International Search Authority, PCT/KR2018/013903, Korean Intellectual Property Office.

* cited by examiner

*Primary Examiner* — Dale R Miller
(74) *Attorney, Agent, or Firm* — Gavrilovich, Dodd & Lindsey LLP

(57) ABSTRACT

The present invention relates to a composition for preventing or treating a neurological disorder, comprising aucubin. Specifically, the present invention relates to a pharmaceutical composition for preventing or treating mental illness, comprising aucubin or a pharmaceutically acceptable salt thereof as an active ingredient, to a food composition, to a method for treating mental illness, and to a composition for maintaining the survival of GABAergic neurons, promoting the regeneration of GABAergic neurons, or preventing the apoptosis of GABAergic neurons.
The aucubin according to the present invention exhibits effects of maintaining the survival of GABAergic neurons, promoting the regeneration of GABAergic neurons, preventing the apoptosis of GABAergic neurons, and promoting the production of GABA which is a neurotransmitter, and thus, the aucubin can be effectively used in the prevention or treatment of mental illnesses such as ADHD or autism, etc, which are caused by the deficiency of GABAergic neurons.

6 Claims, 5 Drawing Sheets

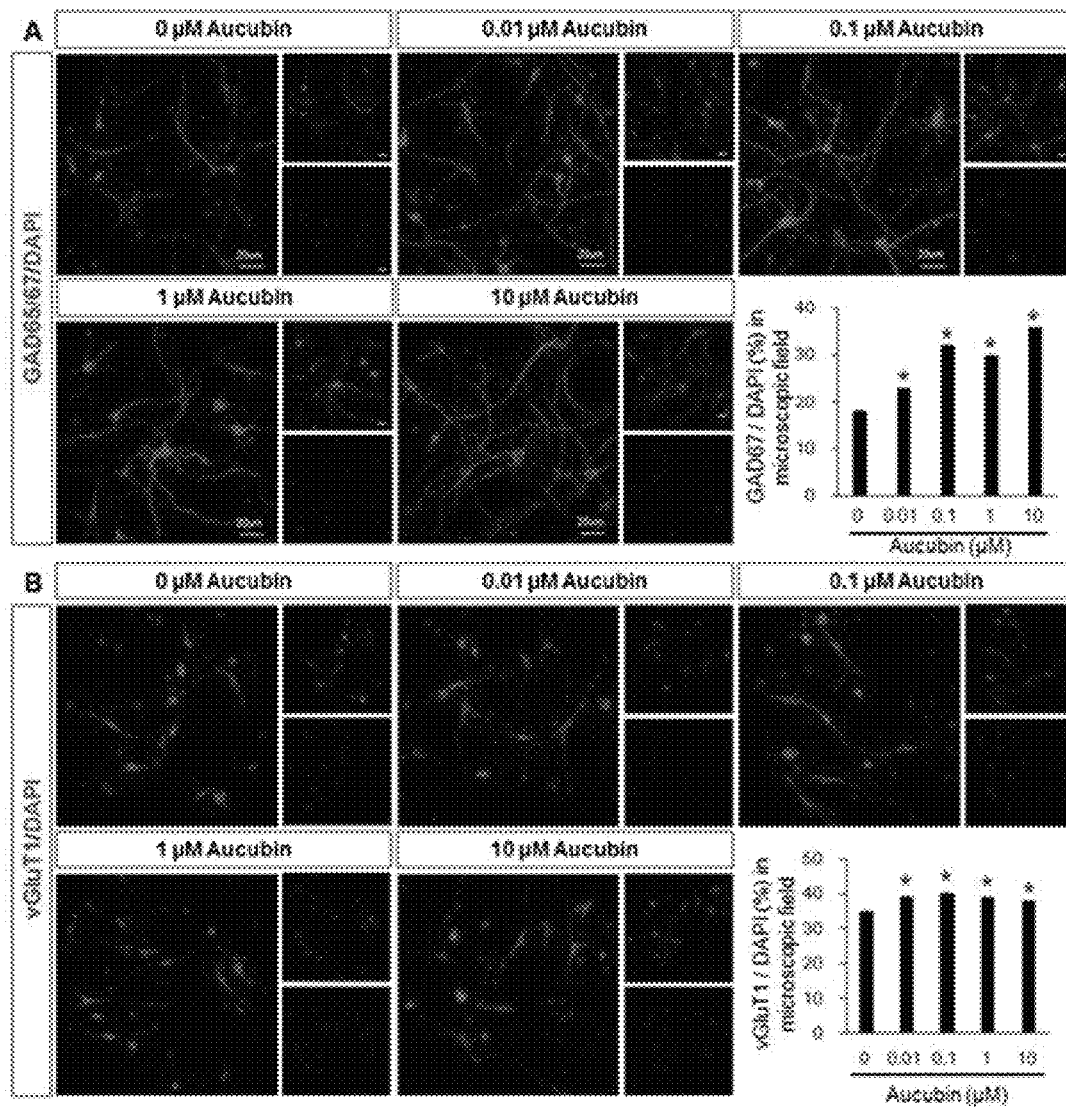
FIG. 1A-B

COMPOSITION FOR PREVENTING OR TREATING NEUROLOGICAL DISORDER COMPRISING AUCUBIN

CROSS REFERENCE TO RELATED APPLICATIONS

This application is a U.S. National Phase Application filed under 35 U.S.C. § 371 and claims priority to International Application No. PCT/KR2018/013903, filed Nov. 14, 2018, which application claims priority under 35 U.S.C. § 119 to Korean Patent Application No. 10-2017-0151768, filed Nov. 14, 2017, the disclosures of which are incorporated herein by reference.

TECHNICAL FIELD

The present invention relates to a composition for preventing or treating a neurological disorder, comprising aucubin. Specifically, the present invention relates to a pharmaceutical composition and a food composition for preventing or treating mental illness, comprising aucubin or a pharmaceutically acceptable salt thereof as an active ingredient; a method for treating mental illness; and a composition for maintaining the survival of GABAergic neurons, promoting the regeneration of GABAergic neurons, or preventing the apoptosis of GABAergic neurons.

BACKGROUND ART

Most common mental illnesses which appear in childhood include attention deficit hyperactivity disorder (ADHD), autism, etc. ADHD is characterized by distraction, excessive activity, and impulsiveness due to continuous lack of attention. A person with ADHD tends to act before thinking, and is very talkative and active. In addition, even if a person with ADHD understands and is aware of rules, the person may not be able to restrain the desire to act hastily. In addition, from before the age of three years old, a child with autism shows aspects of poor language expression-understanding, low attachment to a mother, and low interest in playing with people. Representative symptoms include disabilities in language and communication, stereotypy of repeating certain behaviors, and instabilities in mood and emotion. If such symptoms are left untreated, difficulties persist in many aspects throughout childhood, and in some cases, the symptoms remain even in adolescence and adulthood. ADHD or autism which occurs in children causes loss of the economic population and eventually results in social losses, and thus, the severity of ADHD is more important than that of a degenerative brain disease caused by aging, such as dementia, Alzheimer's disease, etc.

The underlying cause and pathogenesis of ADHD or autism have not been clearly revealed. However, according to some reports, the diseases are considered to be caused by an imbalance between inhibitory neurotransmitters and excitatory neurotransmitters (Giada Cellot, 2014, Front Pediatr., 2: 70). Such imbalance is caused by an imbalance in developmental differentiation of excitatory neurons, which neurodevelopmentally secrete excitatory neurotransmitters, and inhibitory neurons. In fact, it has been reported that in the brain of a patient with autism, the number of inhibitory neurons is about 70% less than that of normal people, and the number of excitatory neurons is about 30% more than that of normal people. Representative examples of inhibitory neurotransmitters and inhibitory neurons secreting the inhibitory neurotransmitters include GABA and GABAergic neurons. Recently, it has been reported that the underlying cause and pathogenesis of ADHD or autism are associated with GABA or GABAergic neurons. (Arch Gen Psychiatry. 2012; 69(7): 750-753; Autism Res. 2017 April; 10(4): 608-619; Neurosci Biobehav Rev. 2012 October; 36(9): 2044-2055; Nature. 2010 Nov. 11; 468(7321): 263-269; Int J Dev Neurosci. 2017 November; 62: 63-72).

Accordingly, in order to treat the mental illnesses above, it would be more effective to use inhibitory neurotransmitters/inhibitory neurons rather than utilizing excitatory neurotransmitters/excitatory neurons, of which the signaling system is complex. Among the inhibitory neurotransmitters/inhibitory neurons, in case of using GABA/GABAergic neurons which are reported to be particularly associated with the underlying cause and pathogenesis of the mental illnesses above, it can treat or prevent the mental illnesses while minimizing side effects since it does not affect the physiological mechanisms related to other inhibitory neurotransmitters/inhibitory neurons.

Meanwhile, there is a method for treating the mental illnesses above by transplanting neural stem cells into the body. However, in this case, the conditions of success are demanding since transplanted stem cells have to be differentiated to form neurons and the neurons that are formed should form a synapse with a target cell in order to survive. Accordingly, there are problems in that many stem cells undergo apoptosis after transplantation and that the effect resulting from the transplantation disappears.

In relation to this, various extracts or compounds, etc., have been developed for the treatment of ADHD or autism, and the examples thereof include a composition for inhibiting autism or a neurodevelopmental disorder, comprising a red ginseng extract as an active ingredient (Korean Patent No. 10-1414133), a compound which is a mGlu2/3 negative allosteric modulator for use in the treatment of autism (Korean Patent No. 10-2015-0070187), etc. However, there has been no development of a composition for treating ADHD or autism, which utilizes the effect of aucubin or a pharmaceutically acceptable salt thereof on GABA or GABAergic neurons.

DISCLOSURE

Technical Problem

The present inventors have made intensive efforts to develop a therapeutic agent for a mental illness such as ADHD or autism, etc. As a result, they have identified that aucubin maintains the survival of GABAergic neurons, promotes the regeneration of GABAergic neurons, and promotes the synthesis of GABA which is a neurotransmitter, and thus, aucubin can be used in treating a mental illness caused by the deficiency of GABA or GABAergic neurons, thereby completing the present invention.

Technical Solution

An object of the present invention is to provide a pharmaceutical composition for preventing or treating mental illness, comprising aucubin or a pharmaceutically acceptable slat thereof as an active ingredient.

Another object of the present invention is to provide a method for treating mental illness, comprising administering the pharmaceutical composition to a subject suspected of having mental illness.

Still another object of the present invention is to provide a food composition for preventing or ameliorating mental illness, comprising aucubin or a physiologically acceptable salt thereof as an active ingredient.

Still another object of the present invention is to provide a composition for maintaining the survival of GABAergic neurons, promoting the regeneration of GABAergic neurons, or preventing the apoptosis of GABAergic neurons, comprising aucubin.

Advantageous Effects

The aucubin according to the present invention exhibits effects of maintaining the survival of GABAergic neurons, promoting the regeneration of GABAergic neurons, preventing the apoptosis of GABAergic neurons, and promoting the production of GABA which is a neurotransmitter, and thus, it can be effectively used in prevention or treatment of a mental illness such as ADHD or autism, etc, which is caused by the deficiency of GABAergic neurons.

BRIEF DESCRIPTION OF DRAWINGS

FIG. 1A-B illustrates immunofluorescence staining images showing the effect of aucubin on maintaining the cell survival of mature GABAergic neurons or glutamatergic neurons, and graphs quantifying the survival rates by counting the number of GABAergic and glutamatergic neurons of the images above. (A) shows a graph quantifying the survival rates of GABAergic neurons expressing a GAD65/67 marker relative to the total number of cells after counting the number of the GABAergic neurons. (B) shows a graph quantifying the survival rates of glutamatergic neurons expressing a vGluT1 marker by counting the number of the glutamatergic neurons. Each value is expressed as the mean±SD of 5 measurements. The statistical significance of the values was confirmed through analysis of variance (ANOVA), and * refers to $p<0.05$ relative to the control group (0 μM) which was not treated with aucubin.

FIG. 2a shows confocal laser microscope-scanned images showing each image and merged image obtained by immunofluorescence staining of GABAergic neurons expressing a GAD65/67 marker (i.e., a GABA-producing enzyme) and cholinergic neurons expressing GFP under the control of the promoter of ChAT (choline acetyltrasnferase) which is an acetylcholine-synthetic enzyme, followed by immunostaining cell nuclei using DAPI. FIG. 2b illustrates a graph quantifying and comparing the survival rates of GABAergic neurons expressing a GAD65/67 marker and cholinergic neurons expressing GFP relative to the total number of cells stained with DAPI after counting the number of the GABAergic neurons and the cholinergic neurons.

Each value is expressed as the mean±SD of 5 measurements. The statistical significance of the values was confirmed through analysis of variance (ANOVA), and * refers that the significance of the increase rate of GABAergic neurons is $p<0.05$ relative to the control group (0 μM) which was not treated with aucubin.

FIG. 3A-D illustrates immunoblot images showing the effect of aucubin on maintaining the survival of mature neurons, GABAergic neurons, or glutamatergic neurons, and graphs quantifying the intensity of the signal of the images above. (A) shows immunoblot images where the levels of expression of GAD65/67, NeuN, VGluT1, and β-actin are respectively detected. (B) quantitatively shows the level of expression of NeuN relative to β-actin, i.e., the level of expression of mature neurons. (C) quantitatively shows the level of expression of GAD65/67 relative to β-actin, i.e., the level of expression of GABAergic neurons. (D) quantitatively shows the level of expression of VGluT1 relative to β-actin, i.e., the level of expression of glutamatergic neurons. Each value is expressed as the mean±SD of 3 measurements. The statistical significance of the values was confirmed through analysis of variance (ANOVA). * refers to $p<0.05$ relative to the control group (0 μM) which was not treated with aucubin, and # refers to $p<0.05$ relative to the experimental group treated with aucubin at a low concentration (0.1 μM).

Figure 4A:
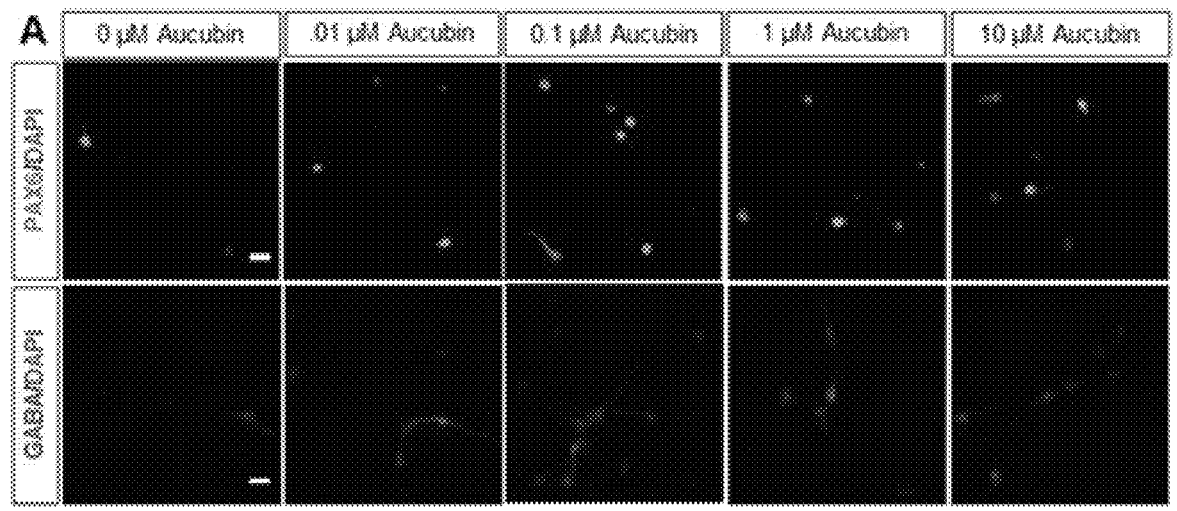
Figure 4B:
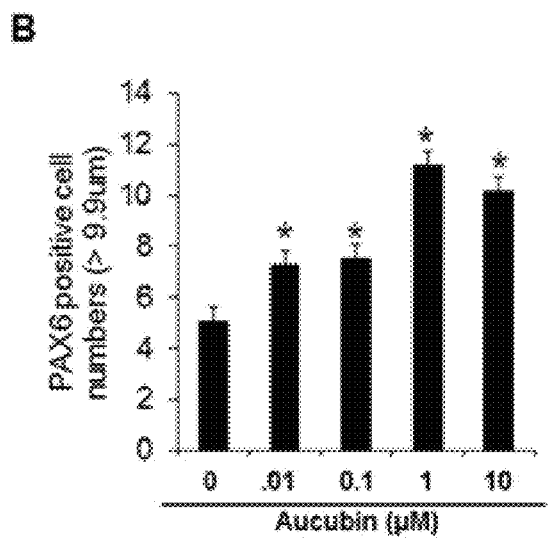
Figure 4C:
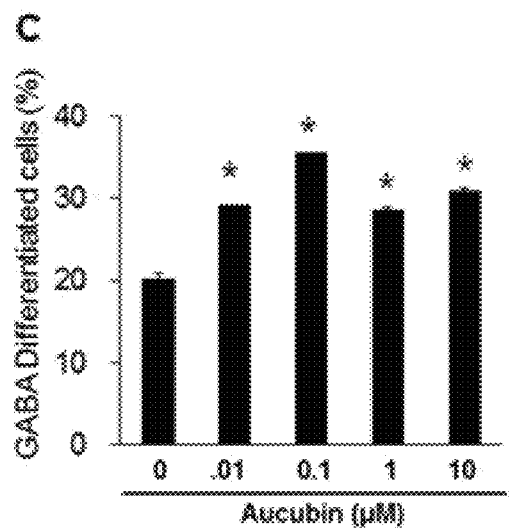

FIG. 4A-C illustrates immunofluorescence staining images showing the effect of aucubin on increasing the amount of GABA produced in a neuronal precursor cell expressing Pax6-GFP, and graphs quantifying the number of GABAergic cells. (A) shows increases in the cell survival rates of precursor cells expressing PAX6-GFP and GABAergic cells producing GABA according to the treatment with aucubin. (B) shows the number of cells expressing a PAX6 marker, and (C) shows the increase in the ratio of the number of cells synthesizing a GABA neurotransmitter relative to the number of cells expressing a PAX6 marker. * refers to $p<0.05$ relative to the control group (0 μM) which was not treated with aucubin, and the scale bar represents 20 μM.

BEST MODE FOR CARRYING OUT THE INVENTION

An aspect of the present invention provides a pharmaceutical composition for preventing or treating a mental illness, comprising aucubin or a pharmaceutically acceptable salt thereof as an active ingredient.

In the present invention, it was confirmed that aucubin increased the number of GABAergic neurons and promoted the production of GABA. Accordingly, the composition of the present invention comprising aucubin can be used very effectively in the prevention and treatment of a mental illness caused by the deficiency of GABAergic neurons and GABA.

As used herein, the term "aucubin" refers to a compound having a structure of Chemical Formula 1 below. Aucubin is included in various plants such as Plantago asiatica, Aucuba japonica, Eucommia ulmoides, Rehmannia glutinosa, Melampyrum roseum, etc., and is known to have various biological activities such as lowering blood pressure and protecting the liver, and as an anti-inflammatory drug, an antimicrobial drug, an analgesic drug, and an anticancer drug (Chang I M, 1983, Drug Chem Toxicol, 6:443-453; Davini M D, 1986, Minerva Chir 41:1531-1535). The aucubin can be synthesized using a synthesis method known in the art, used by isolating and purifying the same from a plant, or obtaining from commercially available ones.

[Chemical Formula 1]

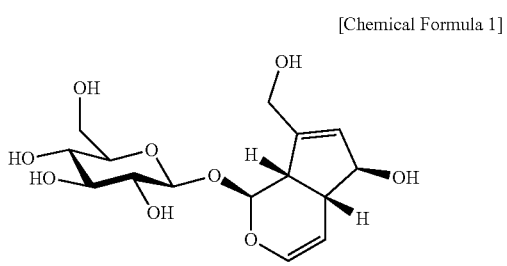

In the present invention, the aucubin may maintain the survival of GABAergic neurons, prevent the apoptosis of GABAergic neurons, increase the number of GABAergic cells by protecting the GABAergic cells from damage, promote the expression of a GABA-producing enzyme, and promote the production of GABA. It is known in the art that aucubin can be applied to the treatment of trauma by promoting axonal regeneration of neurons. However, it has never been known to date that aucubin can exhibit an effect of treating a mental illnesses by maintaining the survival of GABAergic neurons and promoting the production of GABA, and this has been discovered by the present inventors for the first time.

As used herein, the term "GABAergic neurons" refers to inhibitory neurons which secrete γ-aminobutyric acid named "GABA". The GABA is an unique amino acid present only in the brain of mammals, and is known as an inhibitory neurotransmitter of the nervous system.

In addition, as used herein, the term "GABA-producing enzyme" refers to glutamate decarboxylase (GAD) which synthesizes the GABA, and as specific examples, it may be GAD65 and GAD67, but the GABA-producing enzyme is not limited thereto.

In particular, the term "inhibitory neurotransmitter" refers to a substance which inhibits the generation of an action potential of postsynaptic cells through the generation of an inhibitory postsynaptic potential by acting on the postsynaptic membrane of a postsynaptic cell. The term "inhibitory neuron" refers to a neuron which secretes an inhibitory neurotransmitter.

As used herein, the term "mental illness" is named psychosis or a mental disorder. In a broad sense, the term refers to a disease which shows pathological conditions that causes inability to adapt to social life and disrupts daily life by exhibiting abnormalities in mental function. In a narrow sense, the term refers to congenital psychosis, i.e., mental illnesses showing pathological mental conditions except for psychopathia which causes mental retardation or personality deterioration, or psychogenic reaction (neurosis). Specifically, the mental illness may be caused by the deficiency of inhibitory neurons or inhibitory neurotransmitters, and more specifically, it may be attention deficit hyperactivity disorder (ADHD) or autism, but the mental illness is not limited thereto. Further, the mental illness may be a neuropsychiatric disorder. In particular, the term "neuropsychiatric disorder" refers to a mental illness of which the etiology and treatment can be neurologically explained.

The underlying cause and pathogenesis of ADHD or autism are due to an imbalance between inhibitory neurotransmitters and excitatory neurotransmitters. Such imbalance is known to be caused by an imbalance in developmental differentiation of excitatory neurons, which neurodevelopmentally secrete excitatory neurotransmitters, and inhibitory neurons. Recently, it has been reported that the underlying cause or pathogenesis of ADHD or autism is associated with GABA or GABAergic neurons among inhibitory neurotransmitters or inhibitory neurons. Accordingly, in order to treat the mental illness above, it would be more effective to use inhibitory neurotransmitters and inhibitory neurons which secrete the inhibitory neurotransmitters, especially, GABA and GABAergic neurons. Therefore, it is obvious that the composition of the present invention, which comprises aucubin or a pharmaceutically acceptable salt thereof as an active ingredient, would exhibit an effect of preventing or treating a mental illness, i.e, ADHD or autism.

As used herein, the term "prevention" refers to any activity that inhibits or delays the onset of mental illnesses by administration of the composition of the present invention.

As used herein, the term "treatment" refers to any activity associated with the amelioration or advantageous changes in symptoms of a subject suspected of having or suffering from mental illnesses by administration of the composition of the present invention. The subject suspected of having or suffering from mental illnesses may be any subject besides humans.

In a specific embodiment of the present invention, it was confirmed that aucubin maintains the survival of GABAergic neurons and increases the protein expression of a GABA-producing enzyme (GAD) (FIGS. 1 and 2); and maintains the survival of neurons and promotes the synthesis of GABA (i.e., a neurotransmitter of GABAergic neurons) (FIG. 4). This suggests that, since aucubin increases the number of neurons and GABAergic neurons by inhibiting the apoptosis of thereof and maintaining the survival thereof, and since aucubin promotes the synthesis of GABA secreted by GABAergic neurons and the quantitative increase of a GABA-producing enzyme, the aucubin can be effectively used in the treatment of a mental illness such as attention deficit hyperactivity disorder (ADHD) or autism, etc.

As used herein, the term "pharmaceutically acceptable" refers to a property of being non-toxic to cells or humans that are exposed to the composition.

As used herein, the term "pharmaceutically acceptable salt" refers to a salt in the form that can be pharmaceutically used among salts which are substances in which cations and anions are bound by an electrostatic attraction. Specifically, the pharmaceutically acceptable salt may be common metal salts, salts with organic base, salts with inorganic acid, salts with organic acid, salts with basic or acidic amino acid, etc. More specifically, the metal salts may be alkaline metal salts (sodium salts, potassium salts, etc.), alkaline earth metal salts (calcium salts, magnesium salts, barium salts, etc.), aluminum salts, etc., but are not limited thereto; the salts with organic base may be salts with triethylamine, salts with pyridine, salts with picoline, salts with 2,6-lutidine, salts with ethanolamine, salts with diethanolamine, salts with triethanolamine, salts with cyclohexylamine, salts with dicyclohexylamine, salts with N,N-dibenzylethylenediamine, etc., but are not limited thereto; the salts with inorganic acid may be salts with hydrochloric acid, salts with hydrobromic acid, salts with nitric acid, salts with sulfuric acid, salts with phosphoric acid, etc., but are not limited thereto; the salts with organic acid may be salts with formic acid, salts with acetic acid, salts with trifluoroacetic acid, salts with phthalic acid, salts with fumaric acid, salts with oxalic acid, salts with tartaric acid, salts with maleic acid, salts with citric acid, salts with succinic acid, salts with methanesulfonic acid, salts with benzenesulfonic acid, salts with p-toluenesulfonic acid, etc., but are not limited thereto; the salts with basic amino acid may be salts with arginine, salts with lysine, salts with ornithine, etc., but are not limited thereto; and the salts with acidic amino acid may be salts with aspartic acid, salts with glutamic acid, etc., but are not limited thereto.

The pharmaceutical composition of the present invention includes not only a pharmaceutically acceptable salt of aucubin but also all solvates or hydrates, which can be prepared from the pharmaceutically acceptable salt of aucubin, and all possible stereoisomers. In particular, the solvates, hydrates, and stereoisomers of aucubin can be prepared using conventional methods.

In addition, the pharmaceutical composition may further include a pharmaceutically acceptable carrier, an excipient, or a diluent, which is conventionally used in preparation of a pharmaceutical composition. The carrier may include a non-naturally occurring carrier. Specific examples of the carrier, excipient, and diluent may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, or mineral oil, etc., but the specific examples are not limited thereto.

In addition, the pharmaceutical composition may be in formulation of any one selected from the group consisting of tablets, pills, powders, granules, capsules, suspensions, oral solutions, emulsions, syrups, sterile aqueous solutions, non-aqueous solvents, lyophilized formulations, and suppositories, and may be prepared in various oral or parenteral formulations according to each conventional method. For the preparation of these formulations, the pharmaceutical composition may be formulated in combination with a commonly-used diluent or excipient such as a filler, an extender, a binder, a humectant, a disintegrating agent, a surfactant, etc. As solid formulations for oral administration, tablets, pills, powders, granules, capsules, etc., may be used, and these solid formulations may be prepared by mixing at least one excipient, e.g., starch, calcium carbonate, sucrose or lactose, gelatin, etc. In addition to a simple excipient, a lubricant such as magnesium stearate, talc, etc. may be used. As liquid formulations for oral administration, suspensions, oral solutions, emulsions, syrups, etc., may be used, and in addition to a simple diluent such as water or liquid paraffin, various excipients such as humectants, sweeteners, flavoring agents, preservatives, etc., may be used in the liquid preparations. As formulations for parenteral administration, sterile aqueous solutions, non-aqueous solvents, suspensions, emulsions, lyophilized formulations, or suppositories, etc., may be used. As the non-aqueous solvents and suspensions, propylene glycol, polyethylene glycol, vegetable oils such as olive oil, an injectable ester such as ethyl oleate, etc., may be used. As examples of the bases for suppositories, Witepsol, macrogol, Tween 61, cacao butter, laurinum, glycerogelatin, etc., may be used, but are not limited thereto.

Another aspect of the present invention provides a method for treating a mental illness, comprising administering the pharmaceutical composition to a subject suspected of having a mental illness.

In particular, the definitions of the terms "mental illness" and "treatment" are as described above.

As used herein, the term "administration" refers to the introduction of a composition comprising aucubin or a pharmaceutically acceptable salt thereof to a subject using an appropriate method.

As used herein, the term "subject" refers to all animals such as rats, mice, livestock, etc., including humans who have or may develop a neurological disorder. As specific examples, the subject may be mammals including humans.

The pharmaceutical composition of the present invention may be administered in a pharmaceutically effective amount.

The term "pharmaceutically effective amount" refers to an amount sufficient for the treatment of a disease at a reasonable benefit/risk ratio applicable to a medical treatment. In particular, the level of the effective dose may be determined based on the factors including the kind of a subject, severity of illness, age, sex, drug activity, drug sensitivity, administration time, administration route, dissolution rate, duration of treatment, factors including drug(s) to be simultaneously used in combination, and factors well-known in the other medical field.

The pharmaceutical composition may be administered as an individual therapeutic agent, in combination with other therapeutic agent(s), and sequentially or simultaneously with a conventional therapeutic agent(s). In addition, the pharmaceutical composition may be administered in a single dose or multiple doses. It is important to administer an amount to obtain the maximum effect with a minimum amount without adverse effects considering the factors described above, and these factors can easily be determined by one of ordinary skill in the art.

In addition, the pharmaceutical composition may be orally or parenterally administered (e.g., intravenous, subcutaneous, intraperitoneal, or topical application), and a dosage may change according to a patient's condition and weight, degree of disease, a form of drug, and administration route and time, but can be appropriately selected by one of ordinary skill in the art. As specific examples, the pharmaceutical composition may be generally administered at an amount of 0.001 mg/kg to 100 mg/kg, more specifically, 0.05 mg/kg to 20 mg/kg, and most specifically, 0.1 mg/kg to 10 mg/kg once or several times in a day. However, a preferable dosage can be appropriately selected by one of ordinary skill in the art according to a subject's condition and weight, degree of disease, a form of drug, and administration route and time.

Still another aspect of the present provides a food composition for preventing or ameliorating a mental illness, comprising aucubin or a physiologically acceptable salt thereof as an active ingredient.

The food composition of the present invention can be ingested on a daily basis, which makes it possible to expect excellent ameliorating effects on a mental illness. Unlike general medicines, as the food composition uses a natural substance as a raw material, it has an advantage that there are no side effects which may be caused by a long-term intake of a medicine, and thus, the food compositions can be effectively used for the purpose of preventing or ameliorating a mental illness.

As used herein, the term "physiologically acceptable salt" refers to a salt which is physiologically acceptable and which is conventionally used to exhibit a desired effect of a chemical compound to be administered while not causing allergic reactions such as gastrointestinal disorders, dizziness, etc. or similar reactions, when the salt is administered to a living organism.

As used herein, the term "amelioration" refers to any activity that reduces the degree of parameters, e.g., the degree of symptoms, associated with conditions to be treated by administration of the composition.

As used herein, the term "food" includes meats, sausages, bread, chocolate, candies, snacks, confectioneries, pizza, ramen, other noodles, gums, dairy products including ice cream, various soups, beverages, teas, drinks, alcoholic beverages, vitamin complexes, health functional food, and health food, etc., and includes all foods in a common sense.

The health functional food is synonymous with a food for special health use (FoSHU), and refers to a food which has high medical or medicinal effects and which has been processed so that, in addition to nutritional supplementation, biological regulation functions are efficiently exerted. In particular, "function(al)" refers to regulating nutrients with respect to structures and functions of a human body or obtaining beneficial effects, such as physiological actions, which are useful for health use. The health food refers to a food having an effect of actively maintaining or improving health compared to general foods, and a health supplement food refers to a food for health supplement purposes. In some cases, the terms "health functional food", "health food", and "health supplement food" may be interchangeably used.

Specifically, the health functional food refers to a food that is prepared by adding the aucubin of the present invention to food materials such as beverages, teas, spices, gums, confectioneries, etc., or by performing encapsulation, pulverization, suspending, etc. The health functional food refers to a food that brings certain health effects in case of being ingested. However, unlike general medicines, the health functional food uses a food as a raw material, and thus has an advantage that there are no side effects which may be caused by a long-term intake of a medicine.

The food of the present invention can be prepared by a method commonly used in the art, and can be prepared by adding raw materials and ingredients commonly added in the art. In addition, the food composition can be prepared in various types of formulations without limitations as long as the formulation is acceptable as a food.

In addition, the food composition may further include a physiologically acceptable carrier, and the type of carrier is not particularly limited. Any carrier commonly used in the art may be used.

Further, the food composition may include additional ingredients that are commonly used in a food composition to improve odor, taste, visual appearance, etc. For example, vitamins A, C, D, E, B1, B2, B6, B12, niacin, biotin, folate, panthotenic acid, etc. may be included. In addition, minerals such as zinc (Zn), iron (Fe), calcium (Ca), magnesium (Mg), manganese (Mn), copper (Cu), and chromium (Cr), etc.; and amino acids such as lysine, tryptophan, cysteine, valine, etc. may be included.

Further, the food composition may include food additives such as preservatives (potassium sorbate, sodium benzoate, salicylic acid, sodium dehydroacetate, etc.), disinfectants (bleaching powder, high grade bleaching powder, sodium hypochlorite, etc.), antioxidants (butylhydroxyanisole (BHA), butyl hydroxytoluene (BHT), etc.), coloring agents (tar color, etc.), color formers (sodium nitrite, etc.), bleaching agents (sodium sulfite), seasonings (sodium glutamate including MSG, etc.), sweeteners (Dulcin, cyclamate, saccharin, sodium, etc.), flavoring agents (vanillin, lactones, etc.), blowing agents (alum, potassium D-bitartrate, etc.), fortifying agents, emulsifying agents, thickeners (thickening agent), coating agents, gum bases, antifoaming agents, solvents, and modifying agents, etc. The additives may be selected according to the type of food and may be used in appropriate amounts.

Still another aspect of the present invention provides a composition, which comprises aucubin, for maintaining the survival of GABAergic neurons, promoting the regeneration of GABAergic neurons, or preventing the apoptosis of GABAergic neurons.

In particular, the definitions of "aucubin" and "GABAergic neurons" are as described above.

As used herein, the term "survival" refers that neurons function by being survived through protection from neuronal damage or apoptosis. The survival of GABAergic neurons may be maintained by the composition according to the present invention, thereby increasing the number of GABAergic neurons.

As used herein, the term "regeneration" refers that neurons function by being survived through regeneration from neuronal damage or apoptosis. The regeneration of GABAergic neurons may be promoted by the composition according the present invention, thereby increasing the number of GABAergic neurons.

As used herein, the term "apoptosis" refers that neurons die from neuronal damage, etc. If the apoptosis of cells is prevented, the cells can be survived. Accordingly, if the apoptosis of GABAergic neurons is prevented by the composition according to the present invention, the number of the GABAergic neurons may be increased.

In addition, maintaining the survival of the GABAergic neurons, promoting the regeneration of the GABAergic neurons, or preventing the apoptosis of the GABAergic neurons result in a subsequent increase in the expression of a GABA-producing enzyme, which is followed by an increase in the production of GABA (i.e., a neurotransmitter). Accordingly, the composition of the present invention may be a composition, which comprises aucubin, for promoting the production of GABA.

Figure 2A:
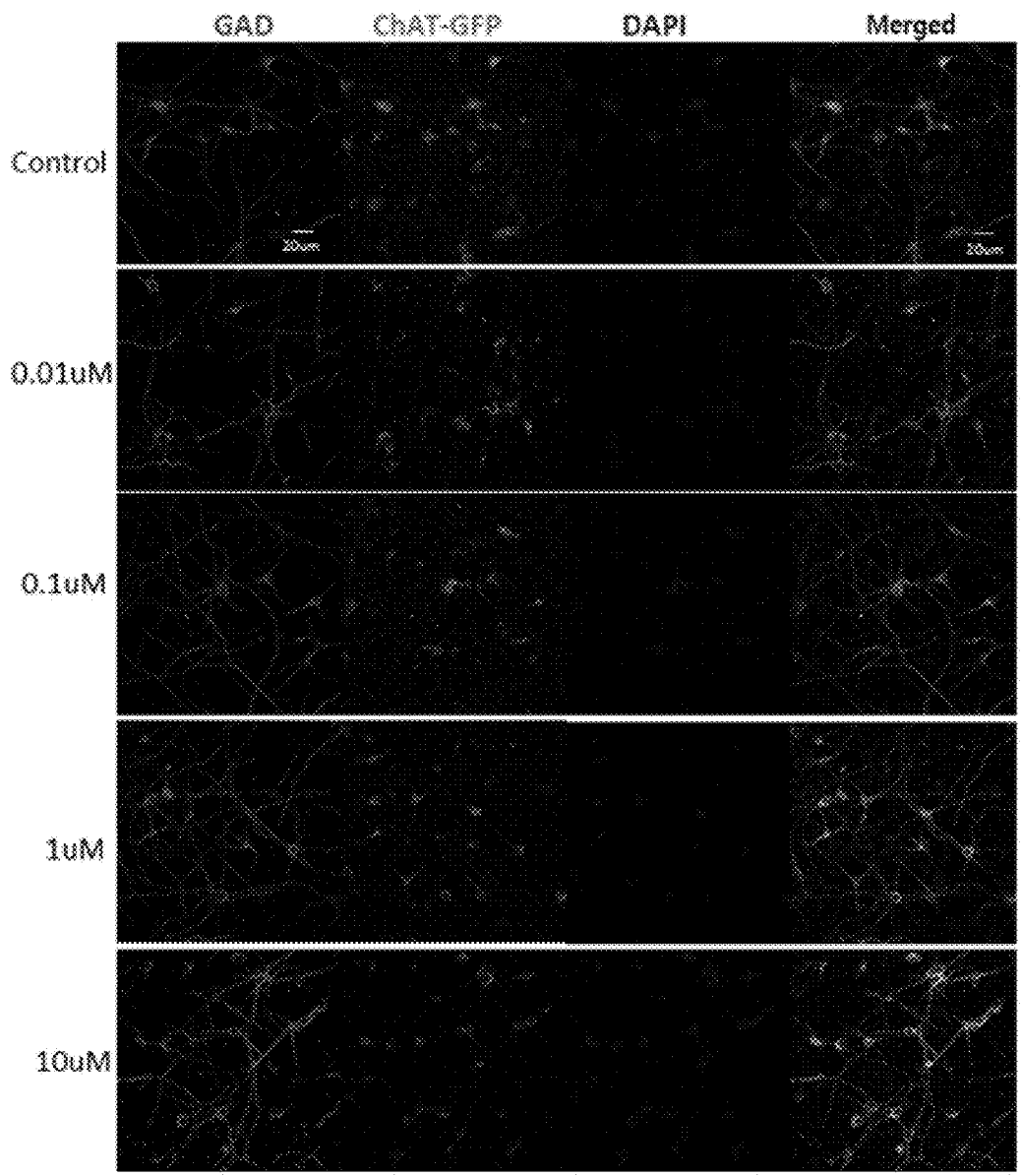
FIG. 2a shows immunofluorescence staining images comparing the effect of aucubin on enhancing the survival of cholinergic neurons expressing GFP and GABAergic neurons expressing GAD in mature neurons cultured in a transgenic mouse brain expressing ChAT-GFP.

In a specific embodiment of the present invention, it was confirmed that aucubin maintains the survival of GABAergic neurons and increases the protein expression of a GABA-producing enzyme (GAD) (FIGS. 1 and 2). Further, it was also confirmed that aucubin maintains the survival of mature neurons expressing NeuN and promotes the synthesis of GABA which is a neurotransmitter of GABAergic neurons (FIG. 4). This suggests that, since aucubin increases the number of neurons and GABAergic neurons by inhibiting the apoptosis thereof and maintaining the survival thereof, and since aucubin promotes the synthesis of GABA, which is a neurotransmitter secreted by GABAergic neurons, and the quantitative increase of a GABA-producing enzyme, the composition of the present invention comprising aucubin can be effectively used for a use in maintaining the survival of GABAergic neurons, promoting the regeneration of GABAergic neurons, preventing the apoptosis of GABAergic neurons, or promoting the production of GABA.

DETAILED DESCRIPTION OF THE INVENTION

Hereinafter, the present invention will be described in detail through exemplary embodiments below. However, these exemplary embodiments are for illustrative purposes only and are not intended to limit the scope of the present invention.

Experimental Example 1

Primary Tissue Culture: Cell Isolation and Culture Method

In order to culture neurons, cells were obtained from the brain of an E16 rat embryo according to a method known in the art (Lim et al., 2007; Jo et al., 2007). Specifically, hippocampal eminence was isolated from the forebrain of the E16 rat embryo, and cells were mechanically isolated from the thus-obtained hippocampal eminence tissue by using $Ca^{2+}/Mg^{2+}$-free HBSS(Hanks' Balanced Salt Solution, Invitrogen). PAX6-GFP expressing neuronal precursor cells (NPCs) were isolated from the sub ventricular zone of a PAX6-GFP transgenic mouse.

The culture of cells was supplemented with 10 ng/mL or 20 ng/mL of bFGF (basic fibroblast growth factor, Invitrogen), and culturing was performed for 3 days in a serum-free N2 medium. After the confluency of cells reaches 70% to 80% by culturing for 3 to 4 days, the cells were subjected to passaging, and then divided and seeded according to an experimental use. Subsequently, the cells were cultured for 7 days in a N2 medium where FGF is removed, allowing neurons to be sufficiently differentiated. The cells were treated with aucubin (Sigma) at varying concentrations (0 μM, 0.01 μM, 0.1 μM, 1 μM, or 10 μM) in a bFGF-free N2 medium.

ChAT-GFP-expressing neuronal precursor cells (NPCs) were isolated from the sub ventricular zone of a CHAT-GFP transgenic mouse which expresses GFP in cholinergic neurons that are differentiated under the control of the promoter of ChAT (choline acetyltransferase) which is an acetylcholine-synthetic enzyme.

Experimental Example 2

Immunofluorescence Staining Analysis

In order to identify the survival rates of mature neurons undergone the primary culture, immunofluorescence staining was performed.

Specifically, cells placed on a 12 mm glass coverslip (Bellco, USA) were fixed with 4% paraformaldehyde for 30 minutes, followed by washing with PBS. Subsequently, the cells were cultured with each of the following primary antibodies: anti-L glutamate (1:100, abcam), anti-eGFP (1:500, Millipore), anti-gamma-aminobutyric acid (anti-GABA, 1:1000, abcam), anti-glutamic acid dehydrogenase 65/67 (anti-GAD65/67, 1:500, Chemicon), or anti-vesicular glutamate transporter1 (vGluT1, 1:500, Chemicon). Thereafter, the cells were cultured with a secondary antibody (1:200, Molecular Probes, Eugene, Oreg.) which is conjugated with Alexa fluor, and DAPI (4,6-di-amidine-2-phenylindole dihydrochloride, 1 μg/mL, Sigma) was used as a counterstaining agent. The negative control group was omitted in the step of culturing the cells with a primary antibody.

The stained cells were observed under a confocal laser scanning biological microscope (LSM 510, Carl Zeiss, Germany). At least 5 random spots (magnification 200×) for each slide were photographed by selecting an average of 5 slides per experimental group, and the number of cells which exhibit a positive response for a neuronal differentiation marker was counted.

For GFP-fluorescence staining, an anti-GFP (rabbit anti-GFP antibody, 1:500, Merck, Germany) primary antibody was used. The statistical analysis was performed by the same method as in Experimental Example 4.

Experimental Example 3

Immunoblot Analysis

In order to identify the type of neurons using a neuronal marker, the relative expression levels of protein markers were compared by immunoblot (western blot) analysis.

Specifically, cells (30,000 cells/cm$^2$), which were cultured in a 60 mm petri dish coated with 15 μg/mL of poly-L-ornithine (Sigma-Aldrich, USA) and 1 μg/mL of fibronectin (Sigma-Aldrich, USA), were used. The cells were lysed using 80 μL of a cold RIPA buffer which includes a protease inhibitor, and then a supernatant including proteins was obtained after performing centrifugation (13,000×g, 10 minutes). The protein quantification was performed using a Bradford protein assay kit (Bio-Rad, Hercules, Calif., USA).

Subsequently, a mixture of 20 μg of the proteins and a loading buffer (Biosesang Co., Seoul, Korea) was boiled at 100° C. for 10 minutes to denature the proteins. The proteins were isolated using 10% polyacrylamide gel electrophoresis, and transferred to a nitrocellulose membrane. The membrane was cultured with each of the following primary antibodies: anti-VGluT1 (1:400, Chemicon), anti-D65/67 (1:500, Chemicon), anti-NeuN (1:5000, abcam), or anti-β-actin (1:1,000, SantaCruz, Del., Calif., USA). Thereafter, signals were detected after culturing the proteins with a secondary antibody.

Experimental Example 4

Statistical Analysis

All quantitative values were expressed as 'mean±standard deviation (SD)'. The significant difference in values was identified through analysis of variance (ANOVA) using the Bonferroni test. It was confirmed that the ANOVA's assumption satisfied the Levene's test for homogeneity of variance, and passed the test for normality. The values of $p<0.05$ were regarded as statistically significant.

Example 1

Identification of Effect of Aucubin on Survival Rates of Neurons

Example 1-1. Identification of Effect of Enhancing Survival Rates of GABAergic Neurons by Immunofluorescence Staining Analysis In order to identify whether aucubin exhibits an effect of maintaining the cell survival of GABAergic neurons and glutamatergic neurons that are cultured, the cells were treated with aucubin, followed by immunofluorescence staining of cells which express a GABAergic neuron-specific marker (GAD65/67). Thereafter, the number of the stained cells was counted and the survival rates thereof were shown in a graph.

Specifically, the cells cultured by the method according to Experimental Example 1 were treated with aucubin at varying concentrations of 0 μM, 0.01 μM, 0.1 μM, 1 μM, and 10 μM, respectively. The number of GABAergic neurons expressing a GAD65/67 marker and the number of glutamatergic neurons expressing a vGluT1 marker were shown in graphs as survival rates relative to the total number of cells.

As a result, as shown in A of FIG. 1, it was identified that when cells were treated with aucubin, the survival rate of GABAergic neurons expressing a GAD67/65 marker (i.e., a GABAergic neuron-specific marker) was increased by up to 2-fold as compared to the cells that were not treated with aucubin.

Meanwhile, as shown in B of FIG. 1, it was identified that the survival rate of excitatory neurons expressing vGluT1, which is a glutamatergic neuron-specific marker, was significantly increased as compared to the cells that were not treated with aucubin. However, it was shown that the increase in the cell survival rate was remarkably lower than the increase in the survival rate of GABAergic neurons expressing GAD67/65.

Based on the results above, it was identified that aucubin of the present invention can increase the number of GABAergic neurons (i.e., inhibitory neuron) rather than that of glutamatergic neurons (i.e., excitatory neuron). This implies that aucubin inhibits the apoptosis of GABAergic neurons during culture to maintain the survival of the GABAergic neurons, thereby increasing the survival rate thereof. Accordingly, it was identified that aucubin can be used in the treatment of a mental illness such as attention deficit hyperactivity disorder (ADHD) or autism, etc., which is caused by the deficiency of GABAergic neurons or GABA.

Example 1-2. Identification of Effect of Enhancing Survival Rates of Cholinergic Neurons Through Immunofluorescence Staining In order to identify whether aucubin exhibits an effect of maintaining the cell survival of GABAergic neurons and cholinergic neurons that are cultured, the cells were treated with aucubin, followed by immunofluorescence staining of cells which express a cholinergic neuron-specific marker. Thereafter, the number of the stained cells was counted, and compared with the number of the cells expressing a GABAergic neuron-specific marker (GAD65/67), and the survival rates thereof were shown in a graph.

Specifically, the cells cultured by the method according to Experimental Example 1 were treated with aucubin at varying concentrations of 0 μM, 0.01 μM, 0.1 μM, 1 μM, and 10 μM, respectively. The number of GABAergic neurons expressing a GAD65/67 marker and the number of cholinergic neuron expressing a ChAT-GFP marker were shown in graphs as survival rates relative to the total number of cells which were fluorescence stained with DAPI.

Figure 2B:
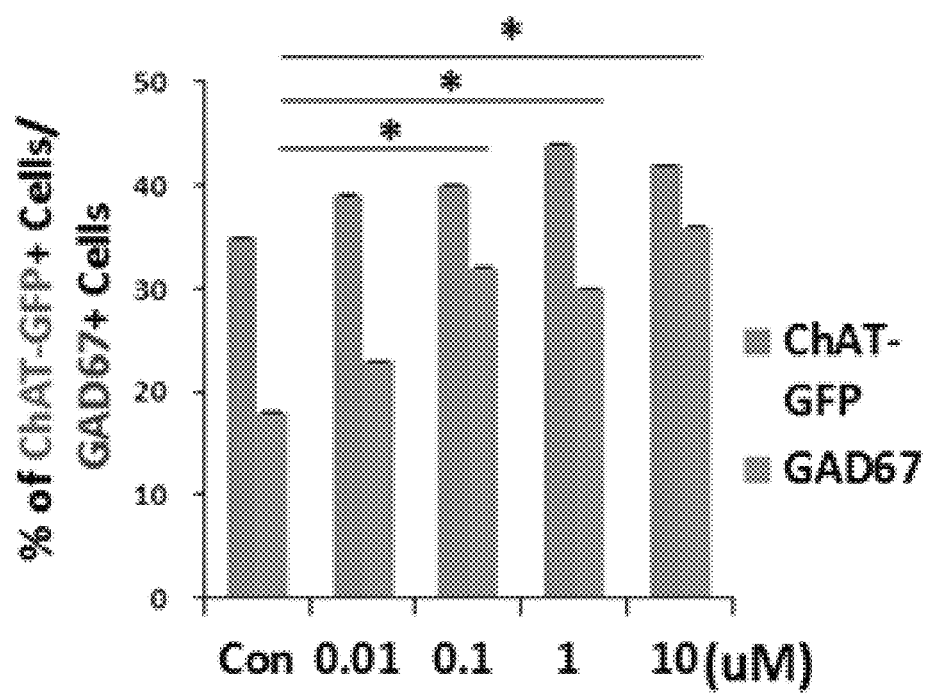
FIG. 2b illustrates a graph quantifying the survival rates of GABAergic and cholinergic neurons of the images above by counting the number of the GABAergic and cholinergic neurons.
Figure 3A:
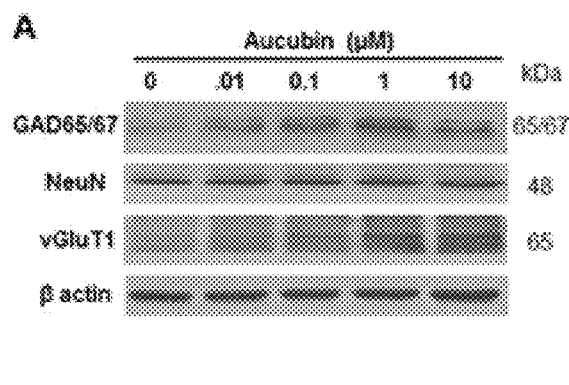
Figure 3B:
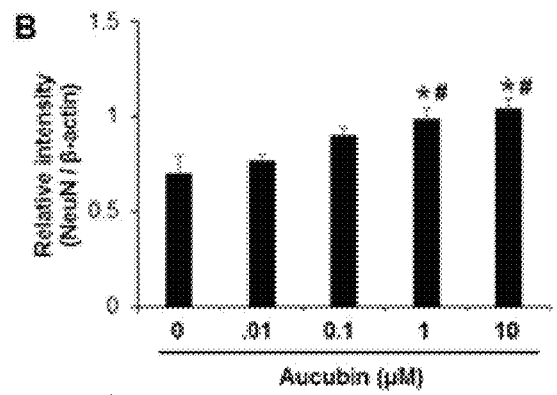
Figure 3C:
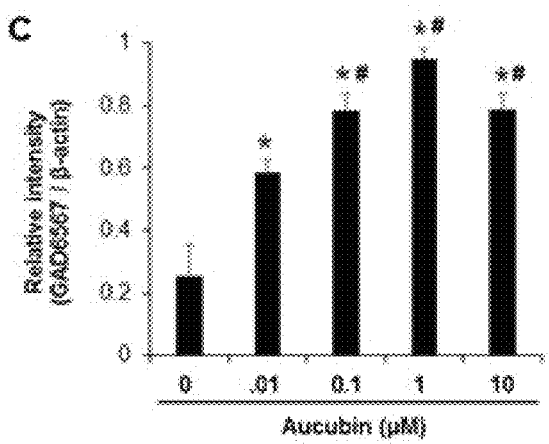
Figure 3D:
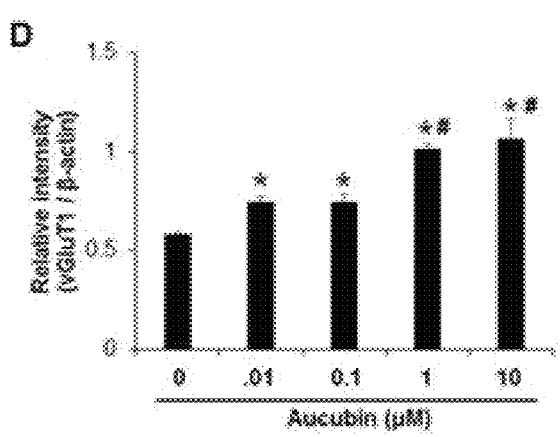

As a result, as shown in FIG. 2b, it was identified that when cells were treated with aucubin, the survival rate of GABAergic neurons expressing a GAD65/67 marker (i.e., a GABAergic neuron-specific marker) was increased by almost 2-fold as compared to the cells that were not treated with aucubin. However, it was shown that the survival rate of cholinergic cells expressing a ChAT-GFP marker was tend to increase to some extent, but the increase rate thereof was not significant. This implies that aucubin does not greatly increase the survival rate of cholinergic neurons similarly to that of glutamatergic neurons, as compared to that of GABAergic neurons.

Example 2

Identification of Effect of Promoting Expression of GABA-producing Enzyme by Immunoblot Analysis In order to verify the effect of aucubin on enhancing the survival rates of GABAergic and glutamatergic neurons, the cells were treated with aucubin, followed by quantifying the expression levels of each cell type marker by an immunoblot method. Specifically, the cells cultured by the method according to Experimental Example 1 were treated with aucubin at various concentrations of 0 μM, 0.01 μM, 0.1 μM, 1 μM, and 10 μM, respectively.

As a result, as shown in A and B of FIG. 3, it was identified that the cells treated with aucubin showed that the expression of NeuN, which is a mature neuron-specific marker, was remarkably increased as compared to the cells that were not treated with aucubin.

In particular, as shown in A and C of FIG. 3, it was identified that the cells treated with aucubin showed that the expression of GAD65/67 which is a GABAergic neuron-specific marker was increased by almost up to 5-fold when the cultured cells were treated with aucubin as compared to the cells that were not treated with aucubin.

Meanwhile, as shown in A and D of FIG. 3, it was identified that the expression of vGluT1 (i.e., a glutamatergic neuron-specific marker) in such cells was significantly increased as compared to the cells that were not treated with aucubin, but the expression level was remarkably lower than the expression level of GAD65/67.

Based on the results above, it was identified that the aucubin of the present invention maintains the survival of neurons to increase the survival rate thereof. In particular, it was identified that aucubin maintains the survival of GABAergic neurons (i.e., inhibitory neurons) rather than that of glutamatergic neurons (i.e., excitatory neurons) and increases the expression of GAD (i.e., a GABA-producing enzyme), thereby increasing the production of GABA.

Accordingly, it was confirmed that aucubin may be effectively used in the treatment of a mental illness such as ADHD or autism, etc., that is caused by the deficiency of GABAergic neurons or GABA.

Example 3

Identification of Effect of Aucubin on Promoting Production of GABA (i.e., Inhibitory Neurotransmitter)

As aucubin increases the survival rate of GABAergic neurons as well as the expression of a GABA-producing enzyme, it was confirmed whether the production of GABA actually increases. After treating the cells with aucubin, the ratio of cells synthesizing GABA was identified through immunofluorescence staining.

Specifically, the neuronal precursor cells, which were isolated from the Pax6-GFP transgenic mouse using the method according to Experimental Example 1, were treated with aucubin at various concentrations of 0 μM, 0.01 μM, 0.1 μM, 1 μM, and 10 μM, respectively.

As a result, as shown in A and B of FIG. 4, it was confirmed that the result of the immunofluorescence staining of the neuronal precursor cells, which express Pax6, with an GFP antibody showed that the cells treated with aucubin increased the number of cells, which express Pax6-GFP, by about 2-fold, and that the ratio of cells synthesizing GABA among the cells expressing Pax6-GFP was increased by 1.5-fold or more as compared to the cells that were not treated with aucubin.

Based on the results above, it was confirmed that the aucubin of the present invention inhibits the apoptosis of GABAergic neurons, increases the survival rate of GABAergic neurons, increases the expression of a GABA-producing enzyme, and promotes the production of GABA which is a neurotransmitter. In addition, it was identified that aucubin can increase the survival rates of neuronal precursor cells and mature neurons, but does not significantly increase the survival rate of glutamatergic neurons.

Accordingly, it was confirmed that aucubin can be usefully used in the treatment of a mental illness such as ADHD or autism, etc., that is caused by the deficiency of GABAergic neurons or GABA.

Based on the results of Examples 1-1, 1-2, 2, and 3, it was identified that since aucubin increases the survival of GABAergic neurons compared to the survival of glutamatergic neurons and cholinergic neurons, and since aucubin promotes the expression of a GABA-sproducingenzyme and the production of GABA, aucubin can be effectively used in the treatment of a mental illness such as ADHD or autism, etc., that is caused by the deficiency of GABAergic neurons.

From the above description, one of ordinary skill in the art will appreciate that the present invention can be implemented in other specific forms without changing the technical spirit or essential features. In this regard, the exemplary embodiments described above are illustrative in all respects and should be understood as not limiting. The scope of the present invention should be construed as including the meaning and scope of the appended claims rather than the detailed description, and all changes or modifications derived from the equivalent concepts.

The invention claimed is:

1. A method for treating attention deficit hyperactivity disorder (ADHD) or autism in a subject in need thereof, comprising administering a composition comprising therapeutically effective amounts of aucubin or a pharmaceutically acceptable salt thereof to treat ADHD or autism.

2. The method of claim 1, wherein the composition maintains the survival of GABAergic neurons or prevents the apoptosis of GABAergic neurons.

3. The method of claim 1, wherein the composition promotes the expression of a GABA-producing enzyme.

4. The method of claim 1, wherein the composition promotes the production of GABA.

5. The method of claim 1, wherein the composition comprises aucubin in an amount of 0.001 wt % to 80 wt % relative to the total weight of the composition.

6. The method of claim 1, wherein the composition further comprises a pharmaceutically acceptable carrier, an excipient, or a diluent.

* * * * *